US008058234B2

(12) United States Patent
Varadhachary et al.

(10) Patent No.: US 8,058,234 B2
(45) Date of Patent: Nov. 15, 2011

(54) LACTOFERRIN AS AN AGENT IN THE PREVENTION OF ORGAN TRANSPLANT REJECTION AND GRAFT-VERSUS-HOST-DISEASE

(75) Inventors: Atul Varadhachary, Houston, TX (US); Federica Pericle, Houston, TX (US)

(73) Assignee: Agennix Incorporated, Houston, TX (US)

( * ) Notice: Subject to any disclaimer, the term of this patent is extended or adjusted under 35 U.S.C. 154(b) by 112 days.

(21) Appl. No.: 12/542,620

(22) Filed: Aug. 17, 2009

(65) Prior Publication Data

US 2009/0318334 A1    Dec. 24, 2009

Related U.S. Application Data

(62) Division of application No. 10/732,429, filed on Dec. 10, 2003, now Pat. No. 7,592,306.

(60) Provisional application No. 60/432,113, filed on Dec. 10, 2002, provisional application No. 60/498,338, filed on Aug. 27, 2003.

(51) Int. Cl.
 *A61K 38/40* (2006.01)
(52) U.S. Cl. .................................. 514/2; 514/6; 514/23
(58) Field of Classification Search .................... None
 See application file for complete search history.

(56) References Cited

U.S. PATENT DOCUMENTS

| | | | |
|---|---|---|---|
| 4,977,137 A | 12/1990 | Nichols et al. | 514/6 |
| 5,006,333 A | 4/1991 | Saifer et al. | 424/78 |
| 5,198,419 A | 3/1993 | Ando et al. | 514/8 |
| 5,571,691 A | 11/1996 | Conneely et al. | 435/69.1 |
| 5,571,697 A | 11/1996 | Conneely et al. | 435/69.7 |
| 5,571,896 A | 11/1996 | Conneely et al. | 530/400 |
| 5,674,495 A | 10/1997 | Bowersock et al. | 424/184.1 |
| 5,712,247 A | 1/1998 | Wu et al. | |
| 5,766,939 A | 6/1998 | Conneely et al. | |
| 5,849,881 A | 12/1998 | Conneely et al. | |
| 5,919,913 A | 7/1999 | Nuyens et al. | |
| 5,955,316 A | 9/1999 | Conneely et al. | |
| 6,066,469 A | 5/2000 | Kruzel et al. | |
| 6,080,559 A | 6/2000 | Conneely et al. | |
| 6,100,054 A | 8/2000 | Conneely et al. | |
| 6,111,081 A | 8/2000 | Conneely et al. | |
| 6,228,614 B1 | 5/2001 | Conneely et al. | |
| 6,277,817 B1 | 8/2001 | Kruzel et al. | |
| 6,333,311 B1 * | 12/2001 | Nuijens et al. | 514/12 |
| 6,399,570 B1 | 6/2002 | Mann | |
| 6,455,687 B1 | 9/2002 | Kruzel et al. | |
| 6,635,447 B1 | 10/2003 | Conneely et al. | |
| 7,592,306 B2 * | 9/2009 | Varadhachary et al. | 514/2 |
| 2002/0072596 A1 | 6/2002 | Ruben et al. | 536/23.5 |
| 2003/0105006 A1 | 6/2003 | Mann | 514/12 |
| 2003/0190303 A1 | 10/2003 | Kimber et al. | 424/78.05 |
| 2004/0009895 A1 | 1/2004 | Varadhachary et al. | 514/6 |
| 2004/0009896 A1 | 1/2004 | Glynn et al. | 514/6 |
| 2004/0023334 A1 | 2/2004 | Prior | 435/69.7 |
| 2004/0082504 A1 | 4/2004 | Varadhachary et al. | 514/6 |
| 2004/0142037 A1 | 7/2004 | Engelmayer et al. | 424/486 |
| 2004/0151784 A1 | 8/2004 | Varadhachary et al. | 424/687 |
| 2004/0152623 A1 | 8/2004 | Varadhachary et al. | 514/6 |
| 2004/0152624 A1 | 8/2004 | Varadhachary et al. | 514/6 |
| 2004/0176276 A1 | 9/2004 | Varadhachary et al. | 514/6 |
| 2005/0004006 A1 | 1/2005 | Engelmayer et al. | 514/6 |
| 2005/0019342 A1 | 1/2005 | Varadhachary et al. | 424/185.1 |
| 2005/0064546 A1 | 3/2005 | Conneely et al. | 435/69.1 |
| 2005/0075277 A1 | 4/2005 | Varadhachary et al. | 514/6 |

FOREIGN PATENT DOCUMENTS

| | | |
|---|---|---|
| EP | 0 426 924 | 5/1991 |
| JP | 7-316069 | 12/1995 |
| WO | WO 2001/72322 | 10/2001 |
| WO | WO 2002/03910 | 1/2002 |

OTHER PUBLICATIONS

Chan et al., "Autoantibody formation after allogeneic bone marrow transplantation: correlation with the reconstitution of CD5+ B cells and occurrence of graft-versus-host disease," *Pathology*, 29(2):184-188, 1997.
Cunha, "Intravenous-to-oral antibiotic switch therapy," *Postgraduate Medicine Online*, 101(4), 1997.
Inoue et al., "Lactoferrin for gut GVHD," *Bone Marrow Transplantation*, 28(11):1091-1092, 2001.
International Preliminary Examination Report issued in International Application No. PCT/US2003/39265, completed Apr. 6, 2006.
International Search Report issued in International Application No. PCT/US2003/39265, mailed Apr. 18, 2005.
Kuby et al., "Transplantation Immunology," *Immunology*, 4th Ed. Freeman and Co., Chapter 21, pp. 517-537, 2000.
Kunzendorf et al., "The Th1-Th2 paradigm in 1998: law of nature or rule with exceptions," *Nephrology Dialysis Transplantation*3, 13:2445-2448, 1998. Mencucci et al., "Ophthalmological aspects in allogenic bone marrow transplantation: Sjögren-like syndrome in graft-versus-host disease," *European Journal of Ophthalmology*, 7(1):13-18, 1997.
Nikolic et al., "Th1 and Th2 mediate acute graft-versus-host disease, each with distinct end-organ targets," *The Journal of Clinical Investigation*, 105(9):1289-1298, 2000.
Perico et al., "Delayed graft function in kidney transplantation," *Lancet*, 364:1814-1827, 2004.
Skolnick and Fetrow, "From genes to protein structure and function: novel applications of computational approaches in the genomic era," *Trends in Biotech.*, 18:34-39, 2000.
Suthanthiran, "Human renal allograft rejection: molecular characterization," *Nephrol Dial Transplant*, 13[Suppl. 1]:21-24, 1998.

\* cited by examiner

*Primary Examiner* — Yunsoo Kim
(74) *Attorney, Agent, or Firm* — Fulbright & Jaworski L.L.P.

(57) ABSTRACT

The present invention relates to methods of using lactoferrin (LF) to treat, prevent or reduce the incidence of organ transplant rejection and graft-versus-host-disease. More particularly, the present invention relates to methods of reducing an immune response against miss-matched transplanted organs such as kidney, heart, lung, liver, pancreas and stem cells by administering a composition of lactoferrin to the recipient patients. In addition, this invention relates to the treatment of bone marrow transplant (BMT) donors with lactoferrin to attenuate the development of graft-versus-host-disease in the recipients. Moreover, this invention relates to the treatment of xenograft organ donors with lactoferrin to attenuate the development of graft rejection in the recipients.

29 Claims, 3 Drawing Sheets

LACTOFERRIN AS AN AGENT IN THE PREVENTION OF ORGAN TRANSPLANT REJECTION AND GRAFT-VERSUS-HOST-DISEASE

CROSS-REFERENCE TO RELATED APPLICATIONS

This application is a divisional of prior application Ser. No. 10/732,429, filed Dec. 10, 2003, which claims priority to U.S. Provisional Application Nos. 60/432,113 filed Dec. 10, 2002 and 60/498,338 filed Aug. 27, 2003, which are incorporated herein by reference.

TECHNICAL FIELD

The present invention relates to methods of using lactoferrin (LF) to treat, prevent or reduce the incidence of organ transplant rejection and graft-versus-host-disease (GVHD). More particularly, the present invention relates to methods of reducing an immune response against miss-matched transplanted organs such as kidney, heart, lung, liver, pancreas, bone marrow and peripheral stem cells by administering a composition of lactoferrin to the recipient patients. Moreover, this invention relates to the treatment of bone marrow or peripheral stem cell transplant donors with lactoferrin to attenuate the development of graft-versus-host-disease in the recipients.

BACKGROUND OF THE INVENTION

According to current estimates, 80,764 people in America are waiting for organ transplantation. All organ-transplanted patients undergo an extensive immunosuppression therapy with drugs, such as cyclosporine (Neoral®, Sandimmune®), prednisone (Novo Prednisone®, Apo Prednisone®), azathioprine (Imuran®), tacrolimus or FK506 (Prograf®), mycophenolate mofetil (CellCept®), OKT3 (Muromorab CO3®, Orthoclone®), or ATGAM & Thymoglobulin. While the use of these drugs has improved the chances for survival in patients receiving organ transplants, three-year mortality rates range from 10-40% and chronic rejection remains a serious issue.

Almost all patients experience at least one episode of rejection following transplant surgery. Chronic rejection is a slow, progressive process that usually begins inside the transplant organ's blood vessels, which are lined by donor cells that interact with host white blood cells in the bloodstream. Over time, as a result of inflammation and rejection reactions, scar tissue can accumulate inside these vessels, reducing or preventing blood flow into the filter and chemical plant portions of the kidney. If blockages become widespread, the organ becomes compromised owing to lack of oxygen and nutrients. Approximately 10 percent of kidney transplants fail each year due to chronic rejection, graft dysfunction and kidney toxicity, causing the patient to need dialysis and often a new organ.

While the current therapies used to combat rejection have resulted in improved transplant outcomes, they are only effective if used on a continuous basis. Consequently, most patients must maintain their regimen of anti-rejection drugs for the rest of their lives. In addition, many of the currently approved drugs are highly toxic and produce severe adverse side effects when used regularly leading to a high rate of patient morbidity following the transplant. Adverse effects from these drugs may include fever, nausea, edema, and a wide range of specific organ toxicity. Because anti-rejection drugs are immunosuppressive, patients also run a high risk of developing concomitant infections. Adverse drug interactions are also common and administration of current medications must be carefully monitored and controlled. Thus, there is a significant unmet need for improved anti-rejection drugs which demonstrate both efficacy and better long-term tolerability.

One key strategy for reducing the risk of organ transplant rejection is to more effectively modulate the body's natural immune response to the new organ. Recent therapeutic strategies to combat organ allograft rejection have focused on T cell signaling pathways and the molecules that comprise them. While some pharmaceuticals have shown promise in blocking acute rejection, chronic graft destruction and permanent allograft acceptance in the absence of continuous immune suppression is problematic. Recent data now suggest T cells hold the key to generation of transplantation tolerance and alleviation of long-term drug intervention.

Lactoferrin is a single chain metal binding glycoprotein. Many cell types, such as monocytes, macrophages, lymphocytes, and brush-border cells in the intestine, are known to have lactoferrin receptors. Lactoferrin is found mainly in external secretions of mucosal epithelia such as breast milk, saliva, tears, bile, and pancreatic fluid and has a wide array of functions related to host immune response mechanisms. For example, lactoferrin has been reported to modulate a number of key cytokines, chemokines or other molecules that control the immune response including IL-2, IL-10, IL-18, INF-γ, TNF-α, MIP3-α and NF Kappa-B among others. In addition, lactoferrin has been shown to modulate the Th1/Th2 immune response pathways as well as activate polymorphonuclear neutrophils (PMN) and regulate granulopoeisis.

Recombinant human lactoferrin has previously been described as being purified after expression in a variety of prokaryotic and eukaryotic organisms including *aspergillus* (U.S. Pat. No. 6,080,559), cattle (U.S. Pat. No. 5,919,913), rice, corn, *Saccharomyces* (U.S. Pat. No. 6,228,614) and *Pichia pastoris* (U.S. Pat. Nos. 6,455,687, 6,277,817, 6,066, 469). Also described are expression systems for the expression of full-length human lactoferrins (e.g., U.S. Pat. No. 6,100,054). In all cases, part of the teaching is expression of the full length cDNA and purification of the intact protein whose N-terminal, after processing of the leader peptide, is the amino acid glycine. Nuijens et al. (U.S. Pat. No. 6,333, 311) separately describe variants of human lactoferrin but their focus is limited to deletion or substitution of arginine residues found in the N-terminal domain of lactoferrin.

The present invention is the first to use a lactoferrin composition as a means of immunosuppressant therapy to prevent organ rejection and graft-versus-host-disease.

BRIEF SUMMARY OF THE INVENTION

The present invention is directed to a method for modulating an immune response against organ transplants, inducing permanent allograft or xenograft acceptance and reducing the incidence of graft-versus-host-disease involved in bone marrow or peripheral stem cells transplantation. The method of treatment involves administration of a lactoferrin composition.

The lactoferrin composition, which is dispersed in a pharmaceutically acceptable carrier, comprises lactoferrin or N-terminal lactoferrin variant in which at least the N-terminal glycine residue is truncated or substituted. The lactoferrin is mammalian lactoferrin, more particularly, the lactoferrin is human or bovine. Yet further, the lactoferrin is recombinant lactoferrin. In specific embodiments, the N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

The amount of the lactoferrin that is administered is about 1 mg to about 20 g per day, more preferably, the amount is about 0.1 g to about 5 g per day. More particularly, the composition is a solution, capsule or a tablet having a lactoferrin concentration of about 0.1% to about 100%.

In further embodiments, a metal chelator dispersed in a pharmaceutically acceptable carrier can also be administered with the lactoferrin composition. Preferred metal chelator include, but are not limited to ethylenediaminetetraacetic acid (EDTA) or [ethylenebis(oxyethylenenitrilo)]tetraacetic acid (EGTA). More preferably, the metal chelator is EDTA. The amount of EDTA that is administered is about 1 ng to about 1 g per day A specific embodiment of the present invention is a method of treating tissue or organ transplant rejection in a recipient comprising the step of administering to the recipient a lactoferrin composition in an effective amount to attenuate the tissue or organ transplant rejection. The tissue is bone marrow or peripheral stem cells. In further embodiments the organ includes, but is not limited to kidney, heart, lung, liver or pancreas. The lactoferrin composition reduces allogeneic immune responses in the recipient. Still further, the lactoferrin composition regulates T cell responses by inducing transplant tolerance in the recipient.

A further embodiment comprises administering any immunosuppressive agent, anti-rejection agent or anti-GVHD therapy in combination with the lactoferrin composition. The immunosuppressive agent can be selected from the group consisting of cyclosporine, prednisone, azathioprine, tacrolimus and mycophenolate mofetil.

In a further embodiment, the lactoferrin composition modulates the mucosal or systemic immune system in a subject by increasing the amount of lactoferrin in the gastrointestinal tract, for example stimulating interleukin-18 or MIP-3-alpha in the gastrointestinal tract. The lactoferrin composition can also regulate the activity of immune cells, for example, but not limited to B and T lymphocytes (e.g., CD4+/CD3+ and CD8+/CD3+ cells), antigen-presenting cells, natural killer cells, macrophages and granulocytes. Still further, the lactoferrin composition down-regulates the production or activity of pro-inflammatory cytokines.

The lactoferrin composition of the present invention can be administered parenterally, for example, subcutaneously, intramuscularly, intraperitoneally, intravenously, intraarterially, intramyocardially, transendocardially, transepicardially, or intrathecally.

In a further embodiment, the lactoferrin composition is administered orally. For oral administration, an antacid in combination with the lactoferrin composition can be administered. The lactoferrin can be formulated in a delayed release formulation. Still further, the lactoferrin composition can be formulated wherein release occurs in the small intestine or in the large intestine.

Another embodiment is a method of preventing tissue or organ transplant rejection in a recipient comprising the step of administering to the recipient a lactoferrin composition in an effective amount to prevent the tissue or organ transplant rejection.

A further embodiment is a method of modulating the immune response against an organ or tissue transplant in a recipient comprising the step of administering to the recipient a lactoferrin composition in an effective mount to modulate the response against the organ or tissue transplant.

Still further, another embodiment is a method of treating graft-versus-host-disease in a recipient comprising the steps of administering to the recipient a lactoferrin composition in an effective amount to attenuate the graft-versus-host-disease in the recipient. The embodiment comprises also treating ex vivo the donor organ or tissue with the lactoferrin composition. The tissue is a stem cell for example, bone marrow or peripheral stem cells.

Another embodiment is a method of treating graft-versus-host-disease by administering a lactoferrin composition to the donor organ or donor tissue prior to transplantation into the recipient.

Another specific embodiment is a method of preventing graft-versus-host-disease in a recipient comprising the steps of administering to the recipient a lactoferrin composition in an amount effective to prevent the graft-versus-host-disease in the recipient. The embodiment comprises also treating ex vivo the donor organ or tissue with the lactoferrin composition. The tissue is a stem cell for example, bone marrow or peripheral stem cells.

Another embodiment is a method of treating tissue or organ transplant rejection in a recipient comprising the step of administering to the donor a lactoferrin composition in an amount effective to attenuate the tissue or organ transplant rejection in the recipient.

Still further, another embodiment is a method of treating xenograft tissue or xenograft organ transplant rejection in a recipient comprising the step of administering to the xenograft donor an effective amount of a lactoferrin composition to attenuate or prevent the tissue or organ transplant rejection in the recipient.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing.

DETAILED DESCRIPTION OF THE INVENTION

It is readily apparent to one skilled in the art that various embodiments and modifications can be made to the invention disclosed in this application without departing from the scope and spirit of the invention.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein, the term "allograft" or "allogeneic" refers to a graft that originates from a genetically non-identical donor of the same species as the recipient.

As used herein, the term "autologous" refers to a graft that originates from the recipient.

The term "chemokine" as used herein refers to small proteins that are involved in stimulating or inhibiting the migration and activation of cells, for example phagocytic cells and lymphocytes. One of skill in the art realizes that chemokines play a central role in inflammatory and immune response processes.

The term "cytokine" as used herein refers to proteins that are made by cells that affect the behavior of other cells, for example stimulate or inhibit cell proliferation. For example, cytokines that are made by lymphocytes are often called lymphokines or interleukins. One of skill in the art realizes that the term cytokine is a generic term used in the literature to refer to proteins that are made by cells that can affect the behavior of other cells.

The term "donor" as used herein refers to the subject that provides the organ and/or tissue transplant or graft to be transplanted into the recipient and/or host.

The term "effective amount" or "therapeutically effective amount" as used herein refers to an amount that results in an improvement or remediation of the symptoms of the disease or condition.

The term "graft" as used herein refers to the tissue and/or organ that is transplanted or implanted into the host or recipient.

The term "graft-versus-host-disease" or "GVHD" as used herein is the pathological reaction that occurs between the host and grafted tissue. The grafted or donor tissue dominates the pathological reaction. Graft-versus-host-disease (GVHD) can be seen following stem cell and/or solid organ transplantation. GVHD occurs in immunocompromised subjects, who when transplanted, receive "passenger" lymphocytes in the transplanted stem cells or solid organ. These lymphocytes recognize the recipient's tissue as foreign. Thus, they attack and mount an inflammatory and destructive response in the recipient. GVHD has a predilection for epithelial tissues, especially skin, liver, and mucosa of the gastrointestinal tract. GVHD subjects are immunocompromised due the fact that prior to transplant of the graft, the subject receives immunosuppressive therapy.

The term "lactoferrin composition" as used herein refers to a composition having lactoferrin, a portion or part of lactoferrin, an N-terminal lactoferrin variant, or a combination thereof.

The term "lactoferrin" or "LF" as used herein refers to native or recombinant lactoferrin. Native lactoferrin can be obtained by purification from mammalian milk or colostrum or from other natural sources. Recombinant lactoferrin (rLF) can be made by recombinant expression or direct production in genetically altered animals, plants, fungi, bacteria, or other prokaryotic or eukaryotic species, or through chemical synthesis.

The term "metal chelator" as used herein refers to a compound which binds metal. Metal chelators that can be used in the present invention include the divalent metal chelators, for example, ethylenediaminetetraacetic acid (EDTA), [ethylenebis (oxyethylenenitrilo)]tetraacetic acid (EGTA), 1,2-bis (2-aminophenoxy)ethane-N,N,N',N'-tetraacetic acid (BAPTA), hydroxyethlene triamine diacetic acid, (HEDTA) or salts thereof.

The term "N-terminal lactoferrin variant" as used herein refers to lactoferrin wherein at least the N-terminal glycine has been truncated and/or substituted. N-terminal lactoferrin variants also include, but are not limited to deletion and/or substitution of one or more N-terminal amino acid residues, for example 1, 2, 3, 4, 5, 6, 7, 8, 9, 10, 11, 12, 13, 14, 15, or 16 N-terminal amino acid residues, etc. Thus, N-terminal lactoferrin variants comprise at least deletions or truncations and/or substitutions of 1 to 16 N-terminal amino acid residues. The deletion and/or substitution of at least the N-terminal glycine of lactoferrin mediates the same biological effects as full-length lactoferrin and/or may enhance lactoferrin's biological activity, for example by stimulating the production of various cytokines (e.g., IL-18, MIP-3α, GM-CSF or IFN-γ) by inhibiting various cytokines, (e.g., IL-2, IL-4, IL-5, IL-10, or TNF-α, and by improving other parameters related to allograft organ acceptance and GVHD.

The term "oral administration" as used herein includes oral, buccal, enteral or intragastric administration.

The term "organ or tissue transplant rejection" as used herein refers to a consequence of organ or tissue transplantation caused by the recipient's or host's immune system in response to the transplanted organ/tissue, which can damage or destroy it. Thus, one of skill in the art realizes that "organ or tissue transplant rejection" is controlled by the host subject.

The term "organ" as used herein refers a group of several tissue types that perform a given function. Exemplary organs include, but are not limited to heart, kidney, liver, pancreas, and lung.

The term "progenitor cell" as used herein refers to a cell that is an undifferentiated cell that is capable of differentiating. One of skill in the art realizes that a progenitor cell is an ancestor cell to progeny descendant cells.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intraocular, subcutaneous or intraarticular administration. Yet further, parenteral administration also includes administration into a surgical field.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The term "preventing" as used herein refers to minimizing, reducing or suppressing the risk of developing a disease state or parameters relating to the disease state or progression or other abnormal or deleterious conditions.

The term "recipient" or "host" as used herein refers to any subject that receives an organ and/or tissue transplant or graft.

The term "stem cells" as used herein refers to "undifferentiated cells" that are capable of proliferation, self-maintenance, production of differentiated cells or regeneration of stem cells may be tissue. In preferred embodiments of the present invention, a stem cell is capable of differentiating into a differentiated cell.

The term "subject" as used herein, is taken to mean any mammalian subject to which a human or bovine lactoferrin composition is administered according to the methods described herein. Thus, a skilled artisan realizes that a mammalian subject, includes, but is not limited to humans, monkeys, horses, pigs, cows, dogs, cats, rats and mice. In a specific embodiment, the methods of the present invention are employed to treat a human subject. Another embodiment includes treating a human subject with organ or bone marrow or peripheral stem cells transplanted according to the then medically established guidelines.

The terms "Th1 cells" and "Th2 cells" as used herein refer to cells defined as subsets of CD4 T-cells that are characterized by the cytokines they produce. These cells are often called helper T-cells. It is also known that extracellular antigens tend to stimulate the production of Th2 cells and intracellular antigens induce Th1 cells. Thus, as used herein, "Th cells" is interchangeable with "helper T-cells". The terms "Th1 cytokines" and "Th2 cytokines" or "Th1/Th2" refer to the cytokines produced respectively by Th1 or Th2 cells.

The term "tissue" as used herein refers to a group or collection of similar cells and the intercellular substance which act together to perform a particular function. Primary tissues include epithelial, connective, muscular and nervous.

The term "treating" and "treatment" as used herein refers to administering to a subject a therapeutically effective amount of a lactoferrin composition so that the subject has an improvement in the parameters related to allograft organ acceptance and GVHD. The improvement is any observable or measurable improvement. Thus, one of skill in the art realizes that a treatment may improve the patient condition, but may not be a complete cure of the disease.

The term "xenogeneic" as used herein refers to grafts, such as tissues, cells or organs that are derived from different species.

The term "xenograft" as used herein refers to a graft that originates from a donor of a species that is different from the recipient. Such donor animal may be genetically modified to reduce the antigenicity of donor organs. Donor species may include pigs and non-human primates.

A. LACTOFERRIN

The lactoferrin used according to the present invention can be obtained through isolation and purification from natural sources, for example, but not limited to mammalian milk. The lactoferrin is preferably mammalian lactoferrin, such as bovine or human lactoferrin. In preferred embodiments, the lactoferrin is produced recombinantly using genetic engineering techniques well known and used in the art, such as recombinant expression or direct production in genetically altered animals, plants or eukaryotes, or chemical synthesis. See, for example, U.S. Pat. Nos. 5,571,896; 5,571,697 and 5,571,691, which are herein incorporated by reference.

In certain aspects, the present invention provides lactoferrin variants having enhanced biological activities over natural LF and or rLF, e.g., the ability to stimulate and/or inhibit cytokines or chemokines. In particular, the invention provides variants of lactoferrin from which at least the N-terminal glycine residue has been substituted and/or truncated. The N-terminal lactoferrin variants may occur naturally or may be modified by the substitution or deletion of one or more amino acids.

The deletional variants can be produced by proteolysis of lactoferrin and/or expression of a polynucleotide encoding a truncated lactoferrin as described in U.S. Pat. No. 6,333,311, which is incorporated herein by reference.

Substitutional variants or replacement variants typically contain the exchange of one amino acid for another at one or more sites within the protein. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, e.g., still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

Still further, it is understood that an amino acid can be substituted for another having a similar hydrophilicity value and still obtains a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

Thus, in the present invention, substitutional variants or replacement can be produced using standard mutagenesis techniques, for example, site-directed mutagenesis as disclosed in U.S. Pat. Nos. 5,220,007; 5,284,760; 5,354,670; 5,366,878; 5,389,514; 5,635,377; 5,789,166, and 6,333,311, which are incorporated herein by reference. It is envisioned that at least the N-terminal glycine amino acid residue can be replaced or substituted with any of the twenty natural occurring amino acids, for example a positively charged amino acid (arginine, lysine, or histidine), a neutral amino acid (alanine, asparagine, cysteine, glutamine, glycine, isoleucine, leucine, methionine, phenylaline, proline, serine, threonine, tryptophan, tyrosine, valine) and/or a negatively charged amino acid (aspartic acid or glutamic acid). Still further, it is contemplated that any amino acid residue within the range of N1 to N16 can be replaced or substituted. It is envisioned that at least up to 16 of the N-terminal amino acids residues can be replaced or substituted as long as the protein retains it biological and/or functional activity, which is stimulating the production of various cytokines, (e.g., IL-18, MIP-3α, GM-CSF or IFN-γ) by inhibiting various cytokines, (e.g., IL-2, IL-4, IL-5, IL-10, and TNF-α) and/or by improving the parameters related to allograft organ acceptance and GVHD. Thus, the N-terminal lactoferrin variants of the present invention are considered functional equivalents of lactoferrin.

In terms of functional equivalents, it is well understood by the skilled artisan that, inherent in the definition of a "biologically functional equivalent" protein is the concept that there is a limit to the number of changes that may be made within a defined portion of the molecule while retaining a molecule with an acceptable level of equivalent biological activity and/or enhancing the biological activity of the lactoferrin molecule. Biologically functional equivalents are thus defined herein as those proteins in which selected amino acids (or codons) may be substituted. Functional activity is defined as the ability of lactoferrin to stimulate or inhibit various cytokines or chemokines and/or by improving the parameters related to allograft organ acceptance and GVHD.

Still further, the N-terminal amino acid residues can be substituted with a modified and/or unusual amino acids. A table of exemplary, but not limiting, modified and/or unusual amino acids is provided herein below.

TABLE 1

Modified and/or Unusual Amino Acids

| Abbr. | Amino Acid |
|---|---|
| Aad | 2-Aminoadipic acid |
| BAad | 3-Aminoadipic acid |
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |

TABLE 1-continued

Modified and/or Unusual Amino Acids

| Abbr. | Amino Acid |
|---|---|
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

The presence and the relative proportion of an N-terminal lactoferrin variants (deletions and/or substitutions) in a preparation of lactoferrin (lactoferrin composition) may be done by determination of the N-terminal amino acid sequence by the process of Edman degradation using standard methods. A relative proportion of N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

In this method, the protein is reacted with phenylisothiocyanate (PITC), which reacts with the amino acid residue at the amino terminus under basic conditions to form a phenylthiocarbamyl derivative (PTC-protein). Trifluoroacetic acid then cleaves off the first amino acid as its anilinothialinone derivative (ATZ-amino acid) and leaves the new amino terminus for the next degradation cycle.

The percentage of N-terminal lactoferrin variant may also be done more precisely by using a Dansylation reaction. Briefly, protein is dansylated using Dansyl chloride reacted with the protein in alkaline conditions (pH 10). Following the Dansylation, the reaction mixtures are dried to pellets, then completely hydrolyzed in 6N HCl. The proportion of N-terminal amino acids are identified by RP HPLC using an in-line fluorometer in comparison with standards made up of known dansylated amino acids.

B. PHARACEUTICAL COMPOSITIONS

The present invention is drawn to a composition comprising lactoferrin that is dispersed in a pharmaceutical carrier. The lactoferrin that is contained in the composition of the present invention comprises lactoferrin or an N-terminal lactoferrin variant in which at least the N−1 terminal glycine residue is truncated or substituted. N-terminal lactoferrin variants include variants that at least lack the N-terminal glycine residue or contain a substitution at the N-terminal glycine residue. The substitution can comprise substituting a natural or artificial amino acid residue for the N-terminal glycine residue. For example, the substitution can comprise substituting a positive amino acid residue or a negative amino acid residue for the N-terminal glycine residue or substituting a neutral amino acid residue other than glycine for the N-terminal glycine residue. Other N-terminal lactoferrin variants include lactoferrin lacking one or more N-terminal residues or having one or more substitutions in the N-terminal. The N-terminal lactoferrin variant comprises at least 1% of the composition, at least 5% of the composition, at least 10% of the composition, at least 25% of the composition, at least 50% of the composition or any range in between.

Yet further, the composition comprises lactoferrin in combination with a metal chelator dispersed in a pharmaceutical carrier. Thus, the present invention is drawn to a lactoferrin composition with or without a metal chelator that is dispersed in a pharmaceutical carrier. One of skill in the art understands that both compositions (e.g., lactoferrin alone or lactoferrin in combination with a metal chelator) are within the scope of the present invention and can be used interchangeably depending upon the type of response that is desired. It is envisioned that the addition of a metal chelator to the lactoferrin composition enhances the sequestering of metal ions and thus strengthens the immune system or enhances the effect of lactoferrin.

Metal chelators that can be used in combination with lactoferrin, include the divalent metal chelators, for example, ethylenediaminetetraacetic acid (EDTA), [ethylenebis(oxyethylenenitrilo)]tetraacetic acid (EGTA), 1,2-bis(2-aminophenoxy)ethane-N,N,N',N'-tetraacetic acid (BAPTA), hydroxyethlene triamine diacetic acid, (HEDTA) or any salts thereof. More preferably, EDTA is used in combination with lactoferrin.

Further in accordance with the present invention, the composition of the present invention suitable for administration is provided in a pharmaceutically acceptable carrier with or without an inert diluent. The carrier should be assimilable and includes liquid, semi-solid, e.g., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof.

In accordance with the present invention, the composition is combined with the carrier in any convenient and practical manner, e.g., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, e.g., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc., proteolytic enzyme inhibitors, and the like. Yet further, it is envisioned that divalent metal chelators, for example EDTA, can also be used to stabilize the composition of the present invention. More preferably, for an orally administered composition, the stabilizer can also include antagonists to the secretion of stomach acids.

The composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the lactoferrin composition to be released and absorbed by specialized cells, e.g., epithelial enterocytes and Peyer's patch M cells.

In another embodiment, a powdered composition is combined with a liquid carrier such as, e.g., water or a saline solution, with or without a stabilizing agent.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Sterile injectable solutions are prepared by incorporating the lactoferrin in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Further, the composition for topical administration which is combined with a semi-solid carrier can be further formulated into a gel ointment. A preferred carrier for the formation of a gel ointment is a gel polymer. Preferred polymers that are used to manufacture a gel composition of the present invention include, but are not limited to carbopol, carboxymethylcellulose, and pluronic polymers. Gel polymers prevent denaturation of the composition in the open skin by serum proteases.

The amount of lactoferrin in the present invention may vary from about 1 ng to about 100 g of lactoferrin, more preferably 1 mg to 20 g per day, most preferably 0.1 g to 5 g. In preferred embodiments, the composition of the present invention comprises a lactoferrin concentration of about 0.1% to about 100%. The lactoferrin composition may comprise lactoferrin or an N-terminal lactoferrin variant in which at least the N–1 terminal glycine residue is truncated and/or substituted.

More preferably, the composition of the present invention also contains metal chelators, for example, but not limited to ethylenediaminetetraacetic acid (EDTA), [ethylenebis(oxyethylenenitrilo)]tetraacetic acid (EGTA), 1,2-bis(2-aminophenoxy)ethane-N,N,N',N'-tetraacetic acid (BAPTA), hydroxyethlene triamine diacetic acid, (HEDTA) or salts thereof. The amount of the metal chelator in the composition may vary from about 1 ng to about 1 g. A preferred metal chelator is EDTA.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject.

C. TREATMENT OF ORGAN TRANSPLANT REJECTION AND GVHD

In accordance with the present invention, the composition provided in any of the above-described pharmaceutical carriers is administered as a therapeutic drug to a subject who has undergone organ transplant (kidney, heart, lung, liver, pancreas, bone marrow, peripheral stem cells) and/or as a prophylactic drug to organ and/or tissue transplant, for example bone marrow (BM) or peripheral stem cell donor cells, to prevent the development of GVHD in recipients and/or to prevent or attenuate transplant rejection in the recipients. One of skill in the art can determine the patients who would potentially benefit from a therapeutic agent that would reduce chronic allograft rejection and toxicity associated with standard therapy, or the development of GVHD. One of skill in the art can determine the therapeutically effective amount of the composition to be administered to a subject based upon several considerations, such as local effects, pharmacodynamics, absorption, metabolism, method of delivery, age, weight, disease severity and response to the therapy.

A further embodiment is treating, preventing or reducing the risk of developing graft-versus-host-disease by administering a lactoferrin composition to the donor organ or donor tissue prior to transplantation into the recipient. It is envisioned that administering the lactoferrin composition to the donor tissue/organ will attenuate the immune cells in the donor/organ and prevent the development of the immune response that is mounted against the recipient's tissue, thus preventing or attenuating GVHD. In further embodiments, the recipient and the donor organ/tissue can be treated with the lactoferrin composition of the present invention.

Additional embodiments of the present invention include a method of treating, preventing or attenuating the severity of tissue or organ transplant rejection in a recipient comprising the step of administering to the donor a lactoferrin composition in an amount sufficient to attenuate the tissue or organ transplant rejection in the recipient. It is envisioned that the lactoferrin composition reduces allogeneic immune responses in the recipient. The lactoferrin composition can also be administered to both the recipient and the donor.

Another embodiment is a method of treating, preventing or attenuating the severity of xenograft tissue or xenograft organ transplant rejection in a recipient comprising the step of administering to the xenograft donor a lactoferrin composition in an amount sufficient to attenuate the tissue or organ transplant rejection in the recipient. The lactoferrin composition can also be administered to both the recipient and the xenograft donor.

In particular embodiments, progenitor cells or stem cells may be isolated from at least one organ, cell, tissue or organism. Stem cells can be isolated from embryonic or nonembryonic donors. The tissues from which the stem cells can be isolated include, for example, but are not limited to the bone marrow, the spleen, the liver, peripheral blood, umbilical cord tissue, umbilical cord blood, adipose tissue or skin. Yet further, tissue grafts may be used in the present invention. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, peripheral stem cells, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, or ascite tissue.

In specific embodiments, an organ is the graft. Organs are comprised of tissues having a special function. Exemplary organs that are used in grafts in the present invention include, but are not limited to heart, kidney, pancreas, lung, or liver.

Oral administration of the composition includes oral, buccal, enteral or intragastric administration. It is also envisioned that the composition may be used as a food additive. For example, the composition is sprinkled on food or added to a liquid prior to ingestion. In further embodiments, the composition is administered in conjunction with an antacid. Thus, an antacid is administered prior or substantially simultaneously with or after oral administration of the composition. The administration of an antacid just prior or immediately following the administration of the composition may help to reduce the degree of inactivation of the lactoferrin in the digestive tract. Examples of appropriate antacids include, but are not limited to, sodium bicarbonate, magnesium oxide, magnesium hydroxide, calcium carbonate, magnesium trisilicate, magnesium carbonate and alumin hydroxide gel.

In addition to oral administration, the lactoferrin composition can also be administered parenterally, which includes, but is not limited to intradermal, subcutaneous, intramuscular, intraperitoneal, intravenous, intraarterial, intramyocardial, transendocardial, transepicardial, intrathecal, and infusion techniques.

In a preferred embodiment of the present invention, the composition is administered in an effective amount to decrease, reduce, inhibit or abrogate chronic allograft rejection and toxicity related to standard therapy. The amount of lactoferrin in the composition may vary from about 1 ng to about 100 g, more preferably, 1 mg to about 20 g. Preferably, the composition that is orally administered contains the range of 0.1 g to 5 g of lactoferrin per day.

In further embodiments, the composition of the present invention also contains metal chelators, for example, but not limited to ethylenediaminetetraacetic acid (EDTA), [ethylenebis(oxyethylenenitrilo)]tetraacetic acid (EGTA), 1,2-bis (2-aminophenoxy)ethane-N,N,N',N'-tetraacetic acid (BAPTA), hydroxyethlene triamine diacetic acid, (HEDTA) or salts thereof. The amount of the metal chelator in the composition may vary from about 1 ng to about 1 g. A preferred metal chelator is EDTA.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known efficacy and toxicity (if any) of the therapeutic formulations.

In specific embodiments, the composition is given in a single dose or multiple doses. The single dose may be administered daily, or multiple times a day, or multiple times a week, or monthly or multiple times a month. In a further embodiment, the lactoferrin is given in a series of doses. The series of doses may be administered daily, or multiple times a day, weekly, or multiple times a week, or monthly, or multiple times a month.

The improvement is any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of an immune response against a graft in the recipient. In further aspects, an improvement can consist of any of the following, for example, increased function of the graft, for example, increased urine output for kidney grafts or decreased jaundice for liver grafts; reduction in inflammation; reduction in general discomfort of the recipient; an overall increased tolerance for the graft. Thus, after administration of lactoferrin, if any of the above conditions improve, then the amount of lactoferrin is considered to be an effective amount.

An improvement in GHVD is also any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of immune response from the donor's cells, tissue and/or organ against the host's tissues. GVHD can be acute or chronic or mild or severe. Improvements in acute symptoms include any of the following, for example, decrease skin rash, decrease diarrhea, increase in liver function, decrease in susceptibility to infection. Improvements in chronic symptoms include, but are not limited to decrease skin rash, decrease dermatitis, decrease hair loss, decrease liver damage, decrease dry eyes and mouth, decrease susceptibility to infections and decrease lung and/or gastrointestinal disorders. Thus, after administration of lactoferrin, if any of the above conditions improve, then the amount of lactoferrin is considered to be an effective amount.

Still yet, a further embodiment is a method of regulating a mucosal immune response in the gastrointestinal tract or a systemic immune response in a subject comprising the step of administering a lactoferrin composition to said subject the composition of the present invention. It is envisioned that lactoferrin stimulates MIP-3α and interleukin-18 in the gastrointestinal tract, which regulates immune responses. For example, interleukin-18 modulates both Th1/Th2 responses. It is known by those of skill in the art that IL-18 plays an important role in allogeneic stem cell transplantation. Pretreatment of allogeneic donors with IL-18 significantly improves survival and reduces clinical and pathological indices of acute GVHD in BMT recipients. Other cytokines may also be enhanced or repressed for example, but not limited to IL-1, IL-2, IL-6, IL10, IL-12 and GM-CSF. It is also envisioned that lactoferrin stimulates Th1/Th2 type-responses through the induction and/or repression of Th1 and Th2 cytokines.

D. COMBINATION TREATMENTS

In order to increase the effectiveness of oral administration of the composition of the present invention, it is desirable to combine these compositions with standard therapy. For example, known immunosuppressant agents are used in combination with the composition of the present invention. Exemplary agents known to prevent organ rejection are T cell modifiers such as cyclosporine (Neoral®, Sandimmune®), prednisone (Novo Prednisone®, Apo Prednisone®), azathioprine (Imuran®), tacrolimus or FK506 (Prograf®), mycophenolate mofetil (CellCept®), OKT3 (Muromorab CO3®, Orthoclone®), ATGAM® & Thymoglobulin® or serine-threonine phosphatase calcineurin (CN) inhibitors. In specific embodiments, the standard or approved treatment of GVHD, which is high doses corticosteroids, primarily high-dose methylprednisolone, is used in combination with the lactoferrin composition of the present invention.

In addition to immunosuppressant other anti-rejection and/or anti-GVHD therapies can be used in combination with the lactoferrin composition of the present invention. For example, therapies for preconditioning and prophylaxis of GVHD include, but are not limited to total body irradiation, cytosine arabinoside, L-phenylalanine mustard, cyclophosphamide, etoposide, triethylene thiophosphoramide, antithymocyte globulin, bisulfan, tacrolimus, methylprednisolone, cyclosporin, or methotrexate. Experimental therapies for treatment of GVHD include, but are not limited to cytokine inhibitors/antagonists (e.g., anti-TNFα antibody); IL-1 receptor antagonist; recombinant IL-1 receptor; inhibitors of T-cell activation (e.g., tacrolimus); antimetabolites (e.g., mycophenolate mofetil); anti-CD3 antibody (Murom nab, OKT3); anti-CD25 antibody; anti-IL2 receptor monoclonal antibody daclizumab; extracorporeal photopheresis using ex vivo 8-methoxypsoralen; anti-thymocyte globulins (Thymoglobulin® or ATGAM®); ABX-CBL or CBL-1; or Visilizumab (Nuvion®).

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination.

E. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1:
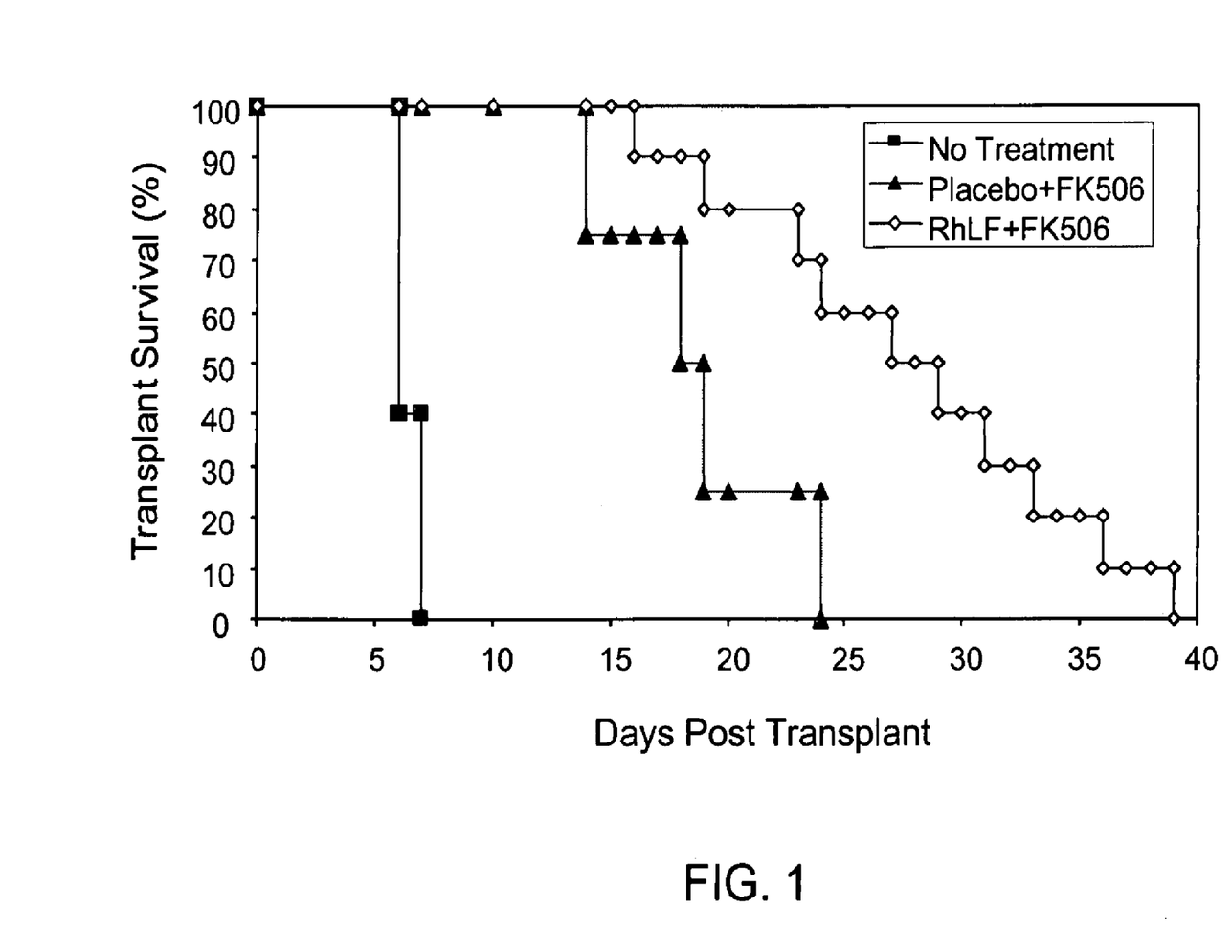
FIG. 1 shows that rhLF in combination with FK506 prolongs heart transplant survival in mice.

RhLF in Combination with Immunosuppressive Drugs Delays Heart Transplant Rejection Hearts were removed from Buffalo rats and transplanted into the abdomen of WF rats using micro vascular surgery. The survival of the transplanted heart was measured daily by palpating for its beat. Transplanted animals either remained untreated (n=5) or were treated with FK506 (0.8 mg/kg once daily×7 days) plus placebo (n=4) or with FK506 (0.8 mg/kg once daily×7 days) plus rhLF (625 mg/kg b.i.d.×14 days followed by 625 mg/kg once daily till rejection; n=7). Drug treatment was started two days prior to the day of transplantation. Average transplant survival of animals treated with FK506 alone (20 days) was not different from animals receiving FK506+placebo (19.3 days) as shown in FIG. 1. RhLF+FK506 was highly statistically different (p<0.01) relative to FK506 alone or FK506+placebo. (See FIG. 1).

Example 2

Figure 2:
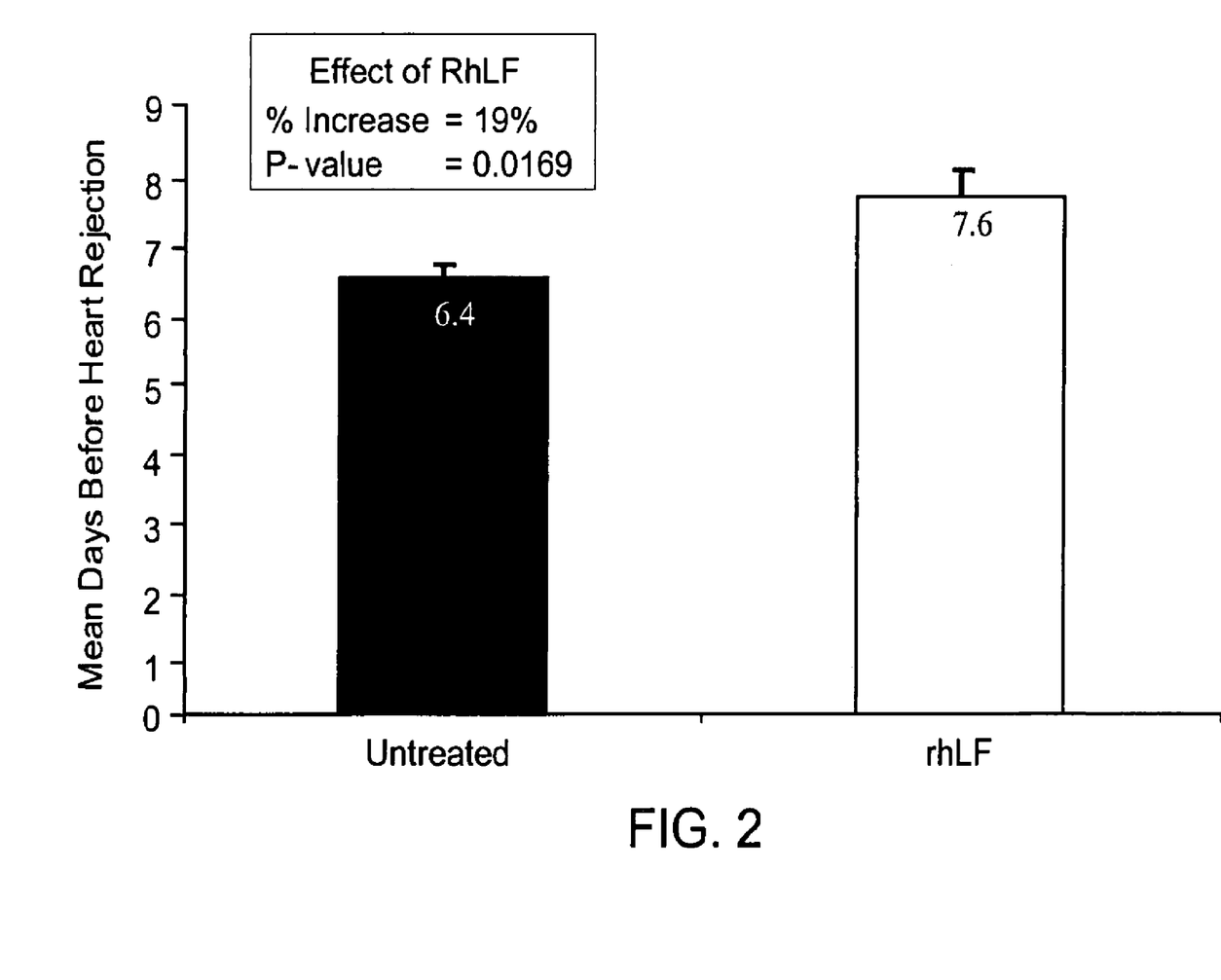
FIG. 2 shows that rhLF prolongs heart allograft survival in mice.

Recombinant Human Lactoferrin (rhLF) Monotherapy Prolongs Allograft Survival Heterotopic heart transplantation in 8-10 weeks old rats (BUF, donor to WF, recipient) was performed using standard microsurgical technique of end-to-side anastomoses to recipient aorta and vena cava. Graft survival was defined as the last day of transabdominally palpable cardiac contractions. Recipients were treated with either placebo or rhLF (625 mg/Kg) for 14 days starting seven days prior to the transplant. FIG. 2 illustrates that lactoferrin alone significantly extended cardiac allograft survival.

Example 3

RhLF Inhibits Kidney Transplant Rejection

Figure 3:
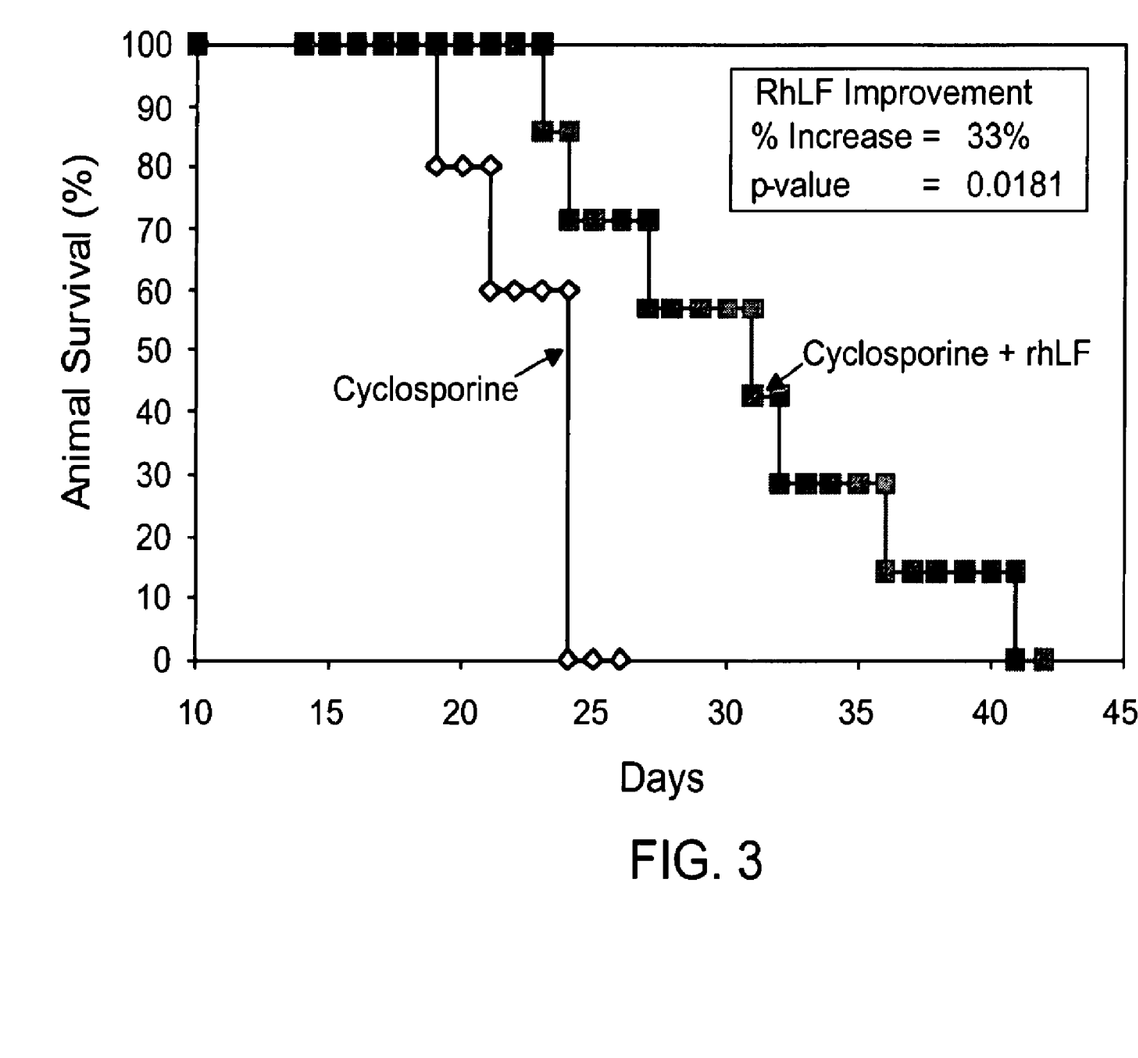
FIG. 3 shows that rhLF in combination with cyclosporine prolongs kidney allograft survival in mice.

The activity of rhLF in combination with cyclosporine (CsA) was determined on kidney allograft survival model in rats. Untreated ACI recipients (RT1a) of Lewis (LEW; RT11) kidney allografts survived a mean survival time (MST) of 8.4±0.6 days (n=5). A 14-day treatment with 1.25 mg/kg CsA extended the survival of kidney allografts to 23.0±2.3 days (n=5). FIG. 3 shows that additional treatment of recipients with oral rhLF on days 3 to 14 with 1250 mg/kg and thereafter with 625 mg/kg prolonged survival to 30.6±3.6 days (n=7; p<0.036). These results demonstrate that additional therapy with lactoferrin provided a beneficial effect for kidney allograft survival.

Example 4

Pre-Treatment of Donors with Recombinant Human Lactoferrin Attenuates Acute Graft-Versus-Host-Disease The effect of pre-treating bone marrow transplantation donors with rhLF on the severity of acute GVHD is tested in a well characterized experimental Balb/c (H2d) in B6 (H2b) GVHD model. Briefly, $2 \times 10^6$ purified donor T cells and $5 \times 10^6$ BM cells from Balb/c mice are injected into TBI (1300 cGy, split into 2 doses separated by 3 h) B6 mice. Donor mice are treated with rhLF (1000 mg/kg) for 8 days before BM transplantation. Pre-treatment of allogeneic BMT donors with rhLF significantly improves survival and reduces clinical and pathologic indices of acute GVHD in BMT recipients.

Example 5

Pre-Treatment of Donor Cell Ex Vivo with Recombinant Human Lactoferrin Attenuates Acute Graft-Versus-Host-Disease The effect of pre-treating bone marrow transplantation donors with rhLF on the severity of acute GVHD is tested in a well characterized experimental Balb/c (H2d) in B6 (H2b) GVHD model. Briefly, $2 \times 10^6$ purified donor T cells and $5 \times 10^6$ BM cells from Balb/c mice are preincubated with rhLF at 10 mg/ml for 3 hours, then infused into B6 mice receiving TBI (1300 cGy, split into 2 doses separated by 3 h). Pre-treatment of allogeneic BMT donor cells with rhLF significantly improves survival and reduces clinical and pathologic indices of acute GVHD in BMT recipients.

Example 6

Allograft Survival Following Organ Treatment is Extended by Ex-Vivo Treatment with rhLF Heterotopic heart transplantation in 8-10 weeks old rats (WF, donor to BUF, recipient) is performed using standard microsurgical technique of end-to-side anastomoses to recipient aorta and vena cava. Graft survival is defined as the last day of transabdominally palpable cardiac contractions. Donor hearts are isolated and pretreated ex vivo with placebo or rhLF at 1 mg/ml or 10 mg/ml for 2 hours or 6 hours before transplantation. The data show that pretreatment of the transplanted organ with lactoferrin significantly extends cardiac allograft survival.

Example 7

Pre-Treatment of Donors with Recombinant Human Lactoferrin Extends Heart Allograft Survival Heterotopic heart transplantation in 8-10 weeks old rats (WF, donor to BUF, recipient) is performed using standard microsurgical technique of end-to-side anastomoses to recipient aorta and vena cava. Graft survival is defined as the last day of transabdominally palpable cardiac contractions. Donor mice are treated with rhLF (1000 mg/kg) for 8 days before organ transplantation. Pre-treatment of allogeneic organ donors with rhLF significantly improves allograft survival.

Example 8

RhLF Improves Kidney Allograft Acceptance

Human patients with kidney transplants are administered rhLF or placebo. The incidence of biopsy-confirmed acute rejection is tested during the first 6 and 12 months post-transplantation and patient survival and graft survival is measured at 12 months post-transplantation.

Example 9

RhLF Improves Kidney Allograft Acceptance in Combination Therapy

Human patients with kidney transplants are administered either cyclosporine plus either rhLF or placebo. The incidence of biopsy-confirmed acute rejection is tested during the first 6 and 12 months post-transplantation and patient survival and graft survival is measured at 12 months post-transplantation. The incidence and severity of renal failure is also measured and compared between the rhLF and placebo treated groups.

Example 10

RhLF Improves Kidney Allograft Acceptance in Combination Therapy

Human patients with kidney transplants are administered either the standard clinical dose of cyclosporine or dose-reduced cyclosporine plus rhLF. The incidence of biopsy-confirmed acute rejection is tested during the first 6 and 12 months post-transplantation and patient survival and graft survival is measured at 12 months post-transplantation. The incidence and severity of renal failure is also measured and compared between the two groups.

Example 11

RhLF Improves Heart Allograft Acceptance

Human patients with heart transplants are administered rhLF or placebo. The incidence of biopsy-confirmed acute rejection is tested during the first 6 and 12 months post-transplantation and patient survival and graft survival is measured at 12 months post-transplantation.

Example 12

RhLF Improves Liver Allograft Acceptance

Human patients with liver transplants are administered rhLF or placebo. The incidence of biopsy-confirmed acute rejection is tested during the first 6 and 12 months post-transplantation and patient survival and graft survival is measured at 12 months post-transplantation.

Example 13

RhLF Improves Lung Allograft Acceptance

Human patients with lung transplants are administered rhLF or placebo. The incidence of biopsy-confirmed acute rejection is tested during the first 6 and 12 months post-transplantation and patient survival and graft survival is measured at 12 months.

Example 14

RhLF Improves Pancreas Allograft Acceptance

Human patients with pancreas transplants are administered rhLF or placebo. The incidence of biopsy-confirmed acute rejection is tested during the first 6 and 12 months post-transplantation and patient survival and graft survival is measured at 12 months.

Example 15

RhLF Treatment of Donors Improves Kidney Allograft Acceptance

Human kidney donors are treated with rhLF 3 mg bid for 14 days before harvesting of kidney for transplant. The incidence of biopsy-confirmed acute rejection is tested in the recipients during the first 6 and 12 months post-transplantation and patient survival, graft survival is measured at 12 months post-transplantation and incidence and dose of cyclosporin use is measured at 12 months.

Example 16

Treatment of Recipients with Recombinant Human Lactoferrin Attenuates Acute Graft-Versus-Host-Disease The effect of prophylactically treating stem cell transplantation recipients with rhLF on the incidence and severity of acute GVHD is tested in a clinical trial. Stem cell recipients receive placebo or rhLF 3 mg bid for 30 days starting one day prior to allogeneic stem cell transplantation. Incidence and severity of acute GVHD and use of steroids and days of hospitalization are evaluated.

Example 17

Treatment of Recipients with Recombinant Human Lactoferrin in Combination Therapy Attenuates Acute Graft-Versus-Host-Disease Patients with acute graft-versus-host-disease are treated with oral corticosteroids plus either rhLF or placebo. The response rate is evaluated in terms of reduction in the severity of acute GVHD, days of hospitalization, incidence of chronic GVHD and 180-day survival.

Example 18

Pre-Treatment of Donors with Recombinant Human Lactoferrin Attenuates Acute Graft-Versus-Host-Disease The effect of pre-treating treating stem cell transplantation donors with rhLF on the subsequent incidence and severity of acute GVHD in the recipients is tested in a clinical trial. Donors receive placebo or rhLF 3 mg bid for 30 days prior to the harvesting of stem cells. Incidence and severity of acute GVHD and use steroids and days of hospitalization in the recipients is evaluated.

REFERENCES CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 5,571,691
U.S. Pat. No. 5,571,697
U.S. Pat. No. 5,571,896
U.S. Pat. No. 5,629,001
U.S. Pat. No. 6,080,559
U.S. Pat. No. 5,919,913
U.S. Pat. No. 6,228,614
U.S. Pat. No. 6,455,687
U.S. Pat. No. 6,277,817
U.S. Pat. No. 6,066,469
U.S. Pat. No. 6,100,054
U.S. Pat. No. 6,333,311

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of treating tissue or organ transplant rejection in a recipient comprising the step of parenterally administering to the recipient an effective amount of a lactoferrin composition to attenuate the tissue or organ transplant rejection.

2. The method of claim 1, wherein said lactoferrin composition reduces allogeneic immune responses in the recipient.

3. The method of claim 1, wherein the tissue is bone marrow or peripheral stem cells.

4. The method of claim 1, wherein the organ is kidney, heart, lung, liver, or pancreas.

5. The method of claim 1, wherein said lactoferrin composition regulates T cell responses by inducing transplant tolerance in the recipient.

6. The method of claim 1, wherein said lactoferrin composition is dispersed in a pharmaceutically acceptable carrier.

7. The method of claim 1, wherein said lactoferrin is mammalian lactoferrin.

8. The method of claim 7, wherein said lactoferrin is human lactoferrin or bovine lactoferrin.

9. The method of claim 1, wherein said lactoferrin is recombinant lactoferrin.

10. The method of claim 1, further comprising administering an antacid in conjunction with said lactoferrin composition.

11. The method of claim 1, further comprising administering the lactoferrin in a delayed release formulation.

12. The method of claim 1, wherein the amount of the lactoferrin composition that is administered is about 1 mg to about 20 g per day.

13. The method of claim 1, wherein the amount of the lactoferrin composition that is administered is about 0.1 g to about 5 g per day.

14. The method of claim 1, wherein said lactoferrin stimulates interleukin-18 or MIP-3-alpha in the gastrointestinal tract.

15. The method of claim 1, wherein said lactoferrin regulates the activity of immune cells.

16. The method of claim 15, wherein the immune cells are B and T lymphocytes, antigen-presenting cells, natural killer cells, macrophages and granulocytes.

17. The method of claim 16, wherein the T lymphocytes are selected from the group consisting of CD4+/CD3+, CD8+/CD3+ cells and NK-T cells.

18. The method of claim 1, wherein said lactoferrin regulates the production or activity of pro-inflammatory cytokines.

19. The method of claim 1, further comprising administering a metal chelator dispersed in a pharmaceutically acceptable carrier.

20. The method of claim 19, wherein the metal chelator is ethylenediaminoetetracacetic acid (EDTA) or [etheylenebis (oxyethylenenitrilo)] tetraacetic acid (EGTA).

21. The method of claim 20, wherein the metal chelator is EDTA.

22. The method of claim 21, wherein the amount of EDTA that is administered is about 1 ng to about 1 g per day.

23. The method of claim 1, further comprising administering an immunosuppressive agent, anti-rejection agent or anti-GVHD therapy in combination with the lactoferrin composition.

24. The method of claim 23, wherein the immunosupressive agent is selected from the group consisting of cyclosporine, prednisone, azathioprine, tacrolimus and mycophenolate mofetil.

25. A method of modulating the immune response against an organ or tissue transplant in a recipient comprising the step of parenterally administering to the recipient an effective amount of a lactoferrin composition to modulate the response against the organ or tissue transplant.

26. A method of treating graft-versus-host-disease in a recipient comprising the step of parenterally administering to the recipient an effective amount of a lactoferrin composition to attenuate the graft-versus-host-disease in the recipient.

27. The method of claim 26 further comprising treating ex vivo the donor organ or tissue with the lactoferrin composition.

28. The method of claim 27, wherein the tissue is a stem cell.

29. The method of claim 27, wherein the tissue is bone marrow or peripheral stem cells.

* * * * *